United States Patent [19]

Bergthaller et al.

[11] B 4,013,468

[45] Mar. 22, 1977

[54] METHOD OF HARDENING A PROTEIN-CONTAINING LAYER OF A SILVER HALIDE PHOTOGRAPHIC MATERIAL WITH AN ALKYL ESTER OF 1,2-DIHYDROQUINOLINE-N-CARBOXYLIC ACID

[75] Inventors: Peter Bergthaller, Cologne; Wolfgang Himmelmann, Opladen; Karl-Wilhelm Schranz, Odenthal-Hahnenberg, all of Germany

[73] Assignee: AGFA-Gevaert, A.G., Leverkusen, Germany

[22] Filed: June 20, 1974

[21] Appl. No.: 481,190

[44] Published under the second Trial Voluntary Protest Program on March 30, 1976 as document No. B 481,190.

[30] Foreign Application Priority Data

June 26, 1973 Germany ............................. 2332317

[52] U.S. Cl. .............................. 96/50 PT; 96/111; 96/74; 260/112 R; 260/117; 106/125; 106/124

[51] Int. Cl.² ........................................... G03C 1/30
[58] Field of Search .................. 96/50 PT, 111, 74; 106/124, 125; 260/117, 112, 287; 424/258

[56] References Cited

UNITED STATES PATENTS 3,389,142  6/1968  Weinberg ........................... 260/287
3,452,140  6/1969  Weinberg ........................... 424/258

Primary Examiner—Won H. Louie, Jr.
Attorney, Agent, or Firm—Connolly and Hutz

[57] ABSTRACT

A process for hardening protein-containing, preferably gelatin-containing, photographic layers wherein as hardeners unsubstituted or substituted esters of 2-substituted, 1,2-dihydroquinoline-N-carboxylic acids and/or unsubstituted or substituted esters of 1-substituted 1,2-dihydroisoquinoline-N-carboxylic acids are used.

11 Claims, No Drawings

METHOD OF HARDENING A PROTEIN-CONTAINING LAYER OF A SILVER HALIDE PHOTOGRAPHIC MATERIAL WITH AN ALKYL ESTER OF 1,2-DIHYDROQUINOLINE-N-CARBOXYLIC ACID

This invention relates to a method of hardening photographic layers which contain protein, preferably gelatine.

Numerous substances have already been described as hardeners for proteins and particularly for gelatine, for example metal salts such as chromium, aluminium or zirconium salts, aldehydes and halogenated aldehyde compounds, particularly formaldehyde, dialdehydes and mucochloric acid, 1,2-and 1,4-diketones such as cyclohexane-1,2-dione and quinones as well as chlorides of dibasic organic acids, anhydrides of tetracarboxylic acids, compounds which contain several reactive vinyl groups such as vinyl sulphones, acrylamides, compounds which contain at least two heterocyclic 3-membered rings which can easily be split open such as ethylene oxide and ethylene imine, polyfunctional methane sulphonic acid esters and bis-α-chloroacylamide compounds.

High-molecular weight hardeners have recently become known, e.g. polyacrolein and its derivatives or copolymers or alginic acid derivatives. These hardeners are used particularly as hardeners which are confined to their own layer.

Many of the compounds mentioned above, however, are unusable, in particular for photographic purposes. Some of these compounds are photographically active and therefore unsuitable for hardening photographic materials while others have such a deleterious effect on the physical properties such as the fragility of the gelatine layers that they are unusable for this reason. Others again give rise to discolourations or changes in pH during the hardening reaction. In addition, for hardening photographic layers it is particularly important that the process of hardening should reach its maximum as soon as possible after drying in order to ensure that the permeability of the hardening material for the developer solution will not constantly change as, for example, in the case of mucochloric acid or formaldehyde.

Some crosslinking agents for gelatine also have a damaging effect on the skin, e.g. ethylene imine compounds, so that they are in any case unsuitable for use on physiological grounds.

It has been known for a long time to use trichlorotriazine and dichloroaminotriazines as hardeners. The disadvantage of these compounds is their relatively high vapour pressure and physiological effect. Water-soluble derivatives which contain carboxyl and sulphonic acid groups and which are obtained by reacting cyanuric chloride with one mol of diaminoalkyl or diaminoaryl sulphonic or carboxylic acid do not have these disadvantages and therefore have been proposed as hardeners in recent times. Their usefulness is, in practice, however, limited by the fact that, due to their high solubility they decompose when left to stand in aqueous solutions and therefore quickly lose their activity. Hydroxy dichlorotriazine has also been proposed as hardener. Lastly, if a hardener is to be suitable for use in photographic layers which contain gelatine it is extremely important both from the point of view of preparation of the photographic material and its processing that it should be possible to predetermine the onset of the crosslinking reaction within certain limits, for example by choice of the drying temperature or choice of the pH.

Compounds which contain two or more acrylic acid amido groups or vinyl sulphone groups in the molecule are also known as hardeners for photographic gelatine layers, for example divinyl sulphone, arylene-bis-vinyl sulphones and N,N',N''-tris-acryloyl-hydrotriazine or methylene-bis-vinyl sulphonamide.

Although the effect of the hardening compounds is satisfactory if allowed to react for some time, the compounds are so sparingly soluble in water that hardening may be uneven within the layer.

The consequences of the undesirable properties of known hardeners described above are extremely important for photographic purposes because important photographic properties such as gradation and sensitivity and, in many cases, also the silver covering power depend on the degree of crosslinking of the layer-forming colloid and undergo changes during storage. Although this disadvantage can be attenuated by a brief after-treatment of the solidified layer with ammonia or an amine, it cannot be completely overcome. To this is added the fact that aliphatic divinyl sulphones have a harmful effect on the skin.

It is an object of this invention to develop rapidly acting hardeners for layers which contain protein and, in particular, gelatine layers for photographic purposes.

A process for hardening protein-containing, preferably gelatine-containing, photographic layers has now been found which is characterised by the use of unsubstituted or substituted esters of 2-substituted 1,2-dihydroquinoline-N-carboxylic acids and/or unsubstituted or substituted esters of 1-substituted 1,2-dihydroisoquinoline-N-carboxylic acids.

Compounds of the following general formulae have proved to be particularly suitable hardeners:

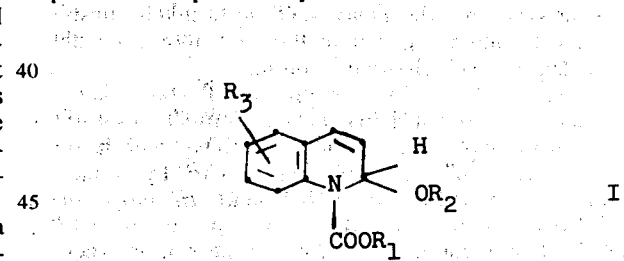

and

II

Table I

| No. | $R_1$ | $R_2$ | $R_3$ | b.p.(°C) | m.p.(°C) |
|---|---|---|---|---|---|
| 1. | $CH_3$ | $CH_3$ | H | 130°(0.3) | |
| 2. | $C_2H_5$ | $C_2H_5$ | H | | 64–66° |
| 3. | $CH_3$ | $C_2H_5$ | H | | 75–76° |
| 4. | $C_2H_5$ | $CH_3$ | H | 135–140°(0.6) | |
| 5. | $CH_3$ | $(CH_2)_2.CH_3$ | H | 135–140°(0.3) | |
| 6. | $CH_3$ | $CH.(CH_3)_2$ | H | 135–140°(0.3) | |
| 7. | $CH_3$ | $(CH_2)_2.OCH_3$ | H | 180–185°(0.4) | |
| 8. | $CH_3$ | $(CH_2)_2.OC_2H_5$ | H | 162–168°(0.6) | |
| 9. | $CH_3$ | $(CH_2)_2.SO_2.CH_3$ | H | non-distillable oil | |
| 10. | $CH_3$ | $(CH_2)_2.SO_2.C_2H_5$ | H | '' '' '' | |
| 11. | $CH_3$ | $(CH_2)_2.Cl$ | H | 135–150°(0.5) | |
| 12. | $CH_3$ | $(CH_2)_2.N^+(CH_3)_3Cl$ | H | | |
| 13. | $C_2H_5$ | $(CH_2)_2.CH_3$ | H | 140–145°(1.0) | |
| 14. | $C_2H_5$ | $CH.(CH_3)_2$ | H | 130–134°(0.5) | |
| 15. | $C_2H_5$ | $(CH_2)_2.OCH_3$ | H | 160–165°(0.25) | |
| 16. | $C_2H_5$ | $(CH_2)_2.OC_2H_5$ | H | 175–180°(0.25) | |
| 17. | $C_2H_5$ | $CH_2.C_6H_5$ | H | 180–185°(0.15) | |
| 18. | $C_2H_5$ | $(CH_2)_2.C_6H_5$ | H | 180–190°(0.15) | |
| 19. | $C_2H_5$ | $(CH_2)_2.SO_2.CH_2.CH_3$ | H | non-distillable oil | |
| 20. | $C_2H_5$ | $(CH_2)_2.Cl$ | H | 135–145°(0.5) | |
| 21. | $C_2H_5$ | $(CH_2)_2.N^+(CH_3)_3Cl$ | H | | 140°(decomp.) |
| 22. | $C_2H_5$ | $(CH_2)_3.CH_3$ | H | 137–139°(0.5) | |
| 23. | $(CH_2)_2.OCH_3$ | $CH_3$ | H | 175–180°(0.3) | |
| 24. | $(CH_2)_2.OCH_3$ | $(CH_2)_2.OCH_3$ | H | 180–185°(0.3) | |
| 25. | $C_2H_5$ | $C_2H_5$ | (5)$SO_3Na$ | Syrup | |
| 26. | $C_2H_5$ | $C_2H_5$ | (8)$OCH_3$ | 160(0.5) | | wherein $R_1$ represents an alkyl group preferably containing 1–4 carbon atoms which may be unsubstituted or substituted with alkoxy, e.g. with methoxy or ethoxy, or with halogen, e.g. with chlorine or bromine, $R_2$ represents an alkyl group preferably containing 1–4 carbon atoms which may be unsubstituted or substituted with alkoxy, e.g. methoxy or ethoxy, with halogen, e.g. chlorine, with dialkylamino, or trialkyl ammonium, e.g. dimethyl- or diethylamino, trimethyl- or triethyl ammonium or with aryl, e.g. phenyl, or with alkyl sulfonyl, e.g. methyl- or ethyl sulfonyl; or, when $R_3$ represents hydrogen, $R_2$ represents

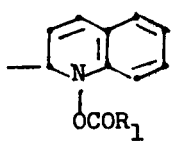

$R_3$ = hydrogen, e.g. chlorine or bromine, alkoxy, e.g. methoxy or ethoxy, alkyl, e.g. methyl, ethyl or propyl, $R_4$ represents a substituted or unsubstituted alkyl group.

The following compounds are given as examples of hardeners of formulae I and II:

Table II

| No. | $R_1$ | $R_4$ | $R_3$ | b.p.(°C) | m.p.(°C) |
|---|---|---|---|---|---|
| 27. | $C_2H_5$ | $CH_3$ | H | 133–136°(1.0) | |
| 28. | $C_2H_5$ | $C_2H_5$ | H | 134–140°(1.0) | |
| 29. | $C_2H_5$ | $CH(CH_3)_2$ | H | 150°(1.0) | |
| 30. | $C_2H_5$ | $C_2H_5$ | (5)$CH_3$ | 150°(0.5) | |

Table III

| No. | $R_1$ | b.p. |
|---|---|---|
| 31. | $C_2H_5$ | — |

The preparation of the compounds is described by Fieser and Fieser in "Reagents for Organic Syntheses", Vol. II, pages 191 et seq. and by J.F. Muren and A. Weidmann in Journal of Medical Chemistry 1971, Vol. 14, No. 1, pages 49–53. Other methods of preparation have been indicated by B. Belleau et al. in J. Am. Chem. Soc. 90, 823–4 (1968) and F. Sipos and D.W. Faston in Synthesis 1971 (6), 321 and have also been described in U.S. Pat. No. 3,389,142 and 3,452,140.

The following examples serve to explain the method of preparation:

1. 2-ethoxy-1(2H)-quinoline carboxylic acid ethyl ester (compound 2):

10.8 g (0.10 mol) of ethyl chloroformate are added dropwise to 12.9 g (0.10 mol) of quinoline under nitrogen. The mixture is stirred for 1 hour at 0° – 7°C, a white precipitate being formed. A solution of 12.9 g (0.10 mol) of diisopropyl ethylamine in 50 mol of absolute alcohol is then added, the precipitate dissolving on addition of this solution. The reaction mixture is now heated to room temperature and evaporated to dryness under vacuum. The residue is treated with 200 ml of cyclohexane, 200 ml of ice-water are added and the organic phase is dried over magnesium sulphate. After evaporation of the solvent, 22.5 g of a pale yellow oil are obtained. Vacuum distillation yeilds 16.9 g of the colourless compound with a boiling point of 115°–118°C (0.1 mm). The oily liquid solidifies when left to stand. Mp. 64°–66°C (from ligroine)

2. 2-hydroxy-N-carbethoxy-1,2-dihydroquinoline and di-(N-carbethoxy-1,2-dihydroxy-2-quinolyl)-ether (compound 31): A cold solution (15°C) of 220 g (2.0 mol) of ethyl chloroformate, 260 g (2.0 mol) of quinoline and 600 ml of dimethylformamide is added to a mixture of 240 g of potassium hydroxide in 400 ml of water and 1600 g of ice over a period of 5 minutes with vigorous stirring. After stirring has been continued for a further 10 minutes, the mixture is extracted with 1 liter of methylene chloride and the extract is washed with water, dried over anhydrous magnesium sulphate, filtered and concentrated by evaporation. 400 g of a pale brown liquid which contains 2-hydroxy-N-carbethoxy-1,2-dihydroquinoline and di-(N-carbethoxy-1,2-dihydro-2-quinolyl)-ether and quinoline (preparation A) are obtained. Unreacted quinoline is removed by distilling 200 g of this oil at a temperature below 100°C (b.p. of quinoline: 60°–80°C, 0.1 mm.Hg). 125 g of a viscous residue which contains 2-hydroxy-N-carbethoxy-1,2-dihydroxy-quinoline and di-(N-carbethoxy-1,2-dihydro-2-quinolyl)-ether are obtained (preparation B).

3. 2-isopropyl-N-carbethoxy-1,2-dihydroquinoline (compound 14): A solution of preparation A described above, 25 ml of isopropanol, 100 ml of diethyl ether and 5 drops of boron trifluoride etherate are stirred for 24 hours at 25°–35°C. The solution is neutralised with saturated sodium bicarbonate solution, diluted with 500 ml of water and extracted twice with 100 ml of diethyl ether. The combined extracts are dried over magnesium sulphate, filtered and concentrated by evaporation. 30 g of an oil are left behind. The oil is distilled and yields 6 g of the compound indicated above, which has a boiling point of 130° – 134°C (0.5 mm.Hg).

4. 2-n-butoxy-N-carbethoxy-1,2-dihydroquinoline (compound 22); 59 g of a solution of the above mentioned preparation A, 50 ml of n-butyl alcohol, 100 ml of diethyl ether and 5 drops of boron trifluoride etherate are stirred for 2 hours at 25°C. After neutralisation with saturated sodium bicarbonate solution (50 ml), the organic phase is separated off and dried over anhydrous magnesium sulphate. An oil is obtained after filtration and concentration by evaporation. The oil is first distilled at 100°C (0.2 ml) to remove low-boiling impurities and the remaining oil is then distilled at 150°C when 2.4 g of the above mentioned compound are obtained. B.p. 137° – 139°C (0.5 mm.Hg).

5. 2-benzyloxy-N-carbethoxy-1,2-dihydroquinoline (compound 17):

A solution of 20 g of preparation A described above, 20 ml of benzyl alcohol, 100 ml of anhydrous diethyl ether and 5 drops of boron trifluoride etherate are stirred for 2 hours at 25°C. The reaction mixture is poured into 100 ml of saturated sodium bicarbonate solution and the ethereal layer is separated off, washed with 100 ml of water and dried over magnesium sulphate. An oil is obtained after filtration and concentration by evaporation. The oil is distilled at 90° – 100°C (0.05 mm.Hg) to remove low-boiling impurities. It is then redistilled to yield 13 g of the above mentioned compound which has a boiling point of 180° – 185°C (0.5 mm.Hg.).

6. 1-ethoxy-2-ethoxycarbonyl-1,2-dihydro-isoquinoline (compound 28):

10.8 g (0.1 mol) of alkyl chloroformate (ethyl chloroformate) are added dropwise to a solution of 12.9 g (0.10 mol) of isoquinoline in 200 ml of methylene chloride at 0°C. 15 ml of ethanol (anhydrous) and 11 g of triethylamine are slowly stirred in at 0°C after 20 minutes. The precipitated salt is filtered off after the addition of 100 ml of toluene and the filtrate is concentrated by evaporation and distilled under vacuum. 12 g of a powerfully light refracting, practically odourless compound which has a melting point of 134° – 140°C at 1.0 mm.Hg are obtained. 10 g of low-boiling impurities are removed with the first runnings of distillation.

The compounds which are to be used according to the invention may be added to the protein layers which are required to be hardened immediately before they are cast, preferably in the form of aqueous or alcoholic solutions. Addition of the compounds shortly before the layers are to be cast is advisable because the compounds react very rapidly with gelatine or any of the other proteins conventionally used in photography. Once the compounds have been added, the casting solutions should be cast within a few minutes. The velocity of the hardening reaction depends mainly on the concentration of the hardening compounds according to the invention in the casting solution.

According to one particularly advantageous procedure, the casting solutions are cast before they have been hardened and the resulting layers are coated with a solution of the hardening compounds, optionally when they are already dry. On the other hand, aqueous and/or alcoholic solutions of the compounds may be bathed into the unhardened or only slightly hardened photographic layers while the photographic material is being processed, for example before development.

The compounds described here may be used either singly or as mixtures. They may advantageously be used for hardening photographic layers which in addition to gelatine also contain as binders other homopolymers and copolymers which contain carboxyl groups. It is assumed that the compounds used according to the invention are capable of bringing about the crosslinking of gelatine and of polymers which contain carboxyl groups.

By photographic layers are meant in this context layers in general which are used for photographic materials, for example light-sensitive silver halide emulsion layers, protective layers, filter layers, antihalation layers, back coatings or any photographic auxiliary layers in general.

The light-sensitive emulsion layers for which the hardening process according to the invention is eminently suitable include, for example, those layers which are based on unsensitised emulsions, X-ray emulsions and other spectrally sensitised emulsions. The hardening process according to the invention is also suitable for hardening the gelatine layers used for various photographic black and white and colour processes. The process according to the invention has proved to be particularly suitable for hardening photographic layer combinations which are used for carrying out colour photographic processes, e.g. those which contain emulsion layers with colour couplers or emulsion layers which are designed to be treated with solutions which contain colour coupler.

The action of the compounds used according to the invention is not impaired by the usual photographic additives. The hardeners are also inert towards photographically active substances such as water-soluble and emulsified water-insoluble colour components, stabilisers, and sensitizers. Furthermore, they have no effect on the light-sensitive silver halide emulsions. Moreover, the compounds can be combined with any compounds taken from the class of hardeners previously known, for example formalin, mucochloric acid, triacrylic formal, bis-vinyl sulphones, bis-vinyl sulphonamides, dialdehydes or bis-chloroacetamides.

The layers may contain water-soluble high-polymer compounds in addition to gelatine, in particular polyvinyl alcohol, polyacrylic acid sodium and other copolymers which contain carboxyl groups, as well as polyvinyl pyrrolidone, polyacrylamide or naturally occurring high-molecular weight substances such as dextrans, dextrins, starch ethers, alginic acid and alginic acid derivatives.

The concentrations at which the hardeners according to the invention are to be used vary within wide limits and depend mainly on the particular hardening compound used.

Satisfactory results are obtained with quantities of preferably 0.5 – 5 % by weight more preferably 1–2 % by weight, based on the dry weight of binder.

As already mentioned above, the hardening reaction between the compounds according to the invention and gelatine or other proteins sets in immediately so that the optimum degree of hardening is reached more or less simultaneously with the drying of the layers following casting or processing.

The effect of the hardening compounds is determined with the aid of the melting point of the layers, which can be found as follows: The layer which has been cast on a substrate is half dipped in water which is continuously heated to 100°C. The temperature at which the layer runs off its substrate (formation of streaks) is taken to be the melting point or melting off point. By this method of measurement, pure protein or gelatine layers which do not contain hardener in no cases show an increase in melting point. The melting off point under these conditions is 30° – 35°C.

Swelling is determined gravimetrically after 10 minutes' treatment in distilled water at 22°C. It is determined by the swelling factor as follows:

$$\frac{\text{Weight of wet layer}}{\text{weight of dry layer}} = \text{swelling factor}$$

To determine the wet scratch resistance, a metal tip of a specified size is passed over a wet layer and loaded with an increasing weight. The wet scratch resistance is indicated by the weight at which the tip leaves a visible scratching trace on the layer. A high weight corresponds to a high wet scratch resistance.

The compounds according to the invention react surprisingly rapidly with proteins so that materials which contain protein can easily be hardened to their optimum degree of hardness within a very short time. This unexpected effect of the compounds is of special importance for the hardening of photographic materials which contain proteins and carboxyl group-containing polymers as binders. The materials can be adjusted to the desired degree of hardness in an easily controlled manner during preparation without requiring prolonged storage times with the concomitant uncertainties of uncontrollable after-hardening.

The hardening compounds used according to the invention are therefore distinguished by a surprisingly rapid hardening reaction which proceeds without aftereffects. This property of the compounds renders them eminently suitable for the preparation of very hard photographic layers with a clearly defined and low degree of swelling. To obtain this result, it is sufficient to treat the dry or only slightly swelled photographic layer with a solution of the hardening compounds for a short time and then to dry them rapidly. Any degree of hardness can easily be obtained in this manner.

EXAMPLE 1

2.5 % solutions of compounds 1, 2, 3, 4, 5, 6, 7, 8, 9, 10, 11, 13, 14, 15, 16, 17, 18, 19, 20, 23 and 24 were prepared by in each case dissolving 2.5 g of the compound in 60 ml of acetone and filling up to a total volume of 100 ml with water.

Two samples of an unhardened gelatine layer $5\mu$ in thickness on a transparent polyethylene terephthalate substrate were dipped into each solution for 1 minute (series A) and 2 further samples were dipped for 3 minutes (series B). From each of the two samples in series A, one was used to determine the melting point of the layer in the wet state and the other to determine the melting point of the layer after 10 minutes' drying at 30°C The solutions were then sealed and kept for 24 hours at 22°C. Two samples of the unhardened gelatine layers were then again dipped into each of the hardening solutions for 1 minute (series C) and another two samples for 3 minutes (series D).

The melting points of the layers in the wet state and after drying were again measured on these two series. The following results were obtained.

| Compound | Layer melting points | | | |
|---|---|---|---|---|
| | Series A | Series B | Series C | Series D |
| 1 | 10'100° | 10'100° | 10'100° | 10'100° |
| 2 | 10'100° | 10'100° | 10'100° | 10'100° |
| 3 | 10'100° | 10'100° | 10'100° | 10'100° |
| 4 | 10'100° | 10'100° | 10'100° | 10'100° |
| 5 | 10'100° | 10'100° | 10'100° | 10'100° |
| 6 | 10'100° | 10'100° | 10'100° | 10'100° |
| 7 | 10'100° | 10'100° | 10'100° | 10'100° |
| 8 | 10'100° | 10'100° | 10'100° | 10'100° |
| 9 | 10'100° | 10'100° | 5'100° | 10'100° |
| 10 | 10'100° | 5'100° | 5'100° | 10'100° |
| 11 | 2'100° | 5'100° | 10'100° | 10'100° |

-continued

| Compound | Layer melting points | | | |
| --- | --- | --- | --- | --- |
| 13 | 10'100° | 10'100° | 10'100° | 10'100° |
| 14 | 90-100° | 90-100° | 10'100° | 10'100° |
| 15 | 10'100° | 10'100° | 10'100° | 10'100° |
| 16 | 10'100° | 10'100° | 10'100° | 10'100° |
| 17 | 47° | 50° | 10'100° | 10'100° |
| 18 | 38° | 50° | 10'100° | 10'100° |
| 19 | 10'100° | 10'100° | 10'100° | 10'100° |
| 20 | 10'100° | 10'100° | 10'100° | 10'100° |
| 23 | 10'100° | 10'100° | 10'100° | 10'100° |
| 24 | 10'100° | 10'100° | 2'100° | 2'100° |

For comparison, 2 samples of the same unhardened gelatine layer were dipped for 1 minute and 3 minutes, respectively, into a 2.5 % solution of tris-acryloyl-hexahydro-s-triazine and mucochloric acid and the layer melting points were determined again as described above.

| Comparison sample | Layer melting points | | | |
| --- | --- | --- | --- | --- |
|  | Series A | Series B | Series C | Series D |
| A | 35°C | 35°C | 35°C | 35°C |
| B | 35°C | 35°C | 35°C | 35°C |

The results show that, compared with conventional hardeners, the new hardeners have a surprisingly rapid and powerful hardening effect and yet are stable in aqueous solution.

EXAMPLE 2

0.5 %, 1 % and 2 % solutions of compounds 1, 2, 3, 4, 7 and 15 were prepared in 1:1 acetone/water.

Strips of an unhardened gelatine layer 5 μ in thickness mounted on a transparent polyethylene terephthalate substrate were dipped into the solutions for 1 minute and dried in air. The layer melting points, swelling factors (10 minutes in water at 20°C) and scratch resistance (30 minutes at 20°C) of the individual samples were determined. The following results were obtained.

| Compound | Concentration of hardening bath | Melting point | Swelling factor | Wet strength (p) |
| --- | --- | --- | --- | --- |
| untreated | — | 38°C | >8 | <300 |
| 1 | 0.5 % | 10'100° | 3.8 | 650 |
|  | 1 % | 10'100° | 2.6 | 950 |
|  | 2 % | 10'100° | 2.2 | 1000 |
| 2 | 0.5 % | 10'100° | 3.4 | 650 |
|  | 1 % | 10'100° | 2.5 | 850 |
|  | 2 % | 10'100° | 2.0 | 950 |
| 3 | 0.5 % | 10'100° | 3.2 | 700 |
|  | 1 % | 10'100° | 2.3 | 950 |
|  | 2 % | 10'100° | 2.0 | 950 |
| 4 | 0.5 % | 10'100° | 3.3 | 750 |
|  | 1 % | 10'100° | 2.3 | 950 |
|  | 2 % | 10'100° | 2.0 | 950 |
| 7 | 0.5 % | 10'100° | 3.4 | 650 |
|  | 1 % | 10'100° | 2.5 | 850 |
|  | 2 % | 10'100° | 2.1 | 1000 |
| 15 | 0.5 % | 10'100° | 3.2 | 550 |
|  | 1 % | 10'100° | 2.5 | 750 |
|  | 2 % | 10'100° | 2.4 | 950 |

The results show that hardening of the gelatine layers, which is invariably resistant to boiling, is associated with a low water absorption (swelling factors below 3.8) and that layers which are hardened with the new hardeners have a high resistance to mechanical action in the wet state. The results also show that the swelling factor and wet strength can be influenced within a wide range by choice of a suitable concentration of hardener without the melting point falling below 100°C.

EXAMPLE 3

Solutions of compounds 1, 2, 3, 4, 7 and 15 (2 % in water/acetone 1:1), which also contain 0.375 % of saponin as wetting agent were applied by the immersion method to 13 μ thick, unhardened silver halide emulsion layers which were mounted on a polyethylene terephthalate substrate and which contain 10 % by weight of gelatine and 18 % by weight, based on the gelatine, of a cyan coupler of the following formula:

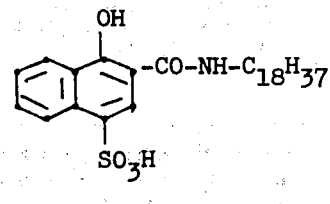

The individual samples were dried and the melting points, swelling factor and wet strength were then determined. For comparison, a gelatine layer 11 μ in thickness which was free from colour coupler was treated with the same solutions of hardeners.

The results shown in the following table were obtained. In the table, series A consists of a layer 13 μ in thickness which contains colour couplers and series B an emulsion layer 11 μ in thickness.

| Compound | Series | Melting point | Swelling factor | Wet strength (p) |
| --- | --- | --- | --- | --- |
| 1 | A | 10'100° | 4.3 | 300 |
|  | B | 10'100° | 3.7 | 300 |
| 2 | A | 10'100° | 5.1 | 250 |
|  | B | 10'100° | 5.6 | 350 |
| 3 | A | 10'100° | 4.7 | 300 |
|  | B | 10'100° | 3.6 | 350 |
| 4 | A | 10'100° | 5.2 | 200 |
|  | B | 10'100° | 4.1 | 350 |
| 7 | A | 10'100° | 5.0 | 300 |
|  | B | 10'100° | 3.4 | 300 |
| 15 | A | 10'100° | 5.4 | 250 |
|  | B | 10'100° | 5.7 | 200 |

The results show that the hardening of the emulsion layers obtained by treating them with solutions of the new hardeners and then drying them is fast to boiling both in those emulsion layers which contain colour couplers and in those which are free from colour couplers. The differences in the swelling factors and wet strengths obtained compared with the values obtained in examples 1 and 2 are due to the shorter time of action of the hardener solutions. The hardening effect is not impaired by the colour coupler dissolved in gelatine. The photographic properties remain unaffected.

EXAMPLE 4

5 samples of an unsensitised silver bromide emulsion layer on a polyethylene backed paper substrate were treated with the following baths as described in example 1:
Sample 1: untreated
Sample 2: bathed for 1 minute in a 2.5 % solution of compound 2 and then dried, Sample 3: bathed for 3 minutes in a 2.5 % solution of compound 2 and then dried,
Sample 4: bathed for 1 minute in a 5 % solution of compound 2 and then dried,
Sample 5: bathed for 3 minutes in a 5 % solution of compound 2 and then dried.

The samples were then exposed behind a step wedge under identical conditions and processed at 25°C as follows:

| Developer | 3 g of hydroquinone<br>1 g of metol<br>13 g of anhydrous sodium sulphite<br>26 g of sodium carbonate, anhydrous,<br>1 g of potassium bromide<br>water up to 1000 ml | 2 minutes at 20°C |
|---|---|---|
| Short stop bath: | 2 % acetic acid solution | 1 minute at 20°C |
| Fixing bath: | 200 g of sodium thiosulphate<br>20 g of potassium metabisulphite<br>water up to 1000 ml | 5 minutes at 20°C |
| Washing: | | 10 minutes at 20°C |

The sensitometric results obtained with the various samples are identical although sample 1 is unhardened and the hardening of the other samples is fast to boiling. The new hardeners are therefore photographically inert and cause no increase in fogging, no reduction in sensitivity and no flattening of the gradation.

EXAMPLE 5

An unhardened multi-layered colour film consisting of
1. a red-sensitive bottom layer 4 μ in thickness which contains 35 g of silver bromide, 80 g of gelatine and 24 g of 1-hydroxy-4-sulpho-2-naphthoic acid heptadecylamide per kg of emulsion,
2. an intermediate layer of gelatine 2 μ in thickness,
3. a green-sensitive middle layer 4 μ in thickness which contains 35 g of silver bromide, 80 g of gelatine and 16 g of 1-(4'-phenoxy-3'-sulpho)-3-heptadecylpyrazolone-5 per kg of emulsion,
4. a yellow filter layer 2 μ in thickness consisting of colloidal silver in gelatine,
5. a blue-sensitive top layer 4 μ in thickness which contains 35 g of silver bromide, 80 g of gelatine and 20 g of 3-stearylamino-benzoylacetyl-5',3'-dicarboxyanilide per kg of emulsion and
6. a protective gelatine layer 2 μ in thickness was cast on a 120 μ thick cellulose triacetate support layer in known manner and dried. The film was coated with a 1 % solution and a 2 % solution of compounds 8 and 24 in water/methanol 4:1.

The layer melting points and temperatures at which the layers become detached were determined immediately after drying.

| Compound: | | Layer detached at | Melting point |
|---|---|---|---|
| 8 | 1 % | 70 - 90°C | 10'100° |
| | 2 % | 80 - 100°C | 10'100° |
| 24 | 1 % | 100°C | 10'100° |
| | 2 % | 95°C | 10'100° |
| Comparison material not covered with top coating | | 38 - 40°C | 42° |

The results show that the multi-layered material has been hardened right through its thickness.

EXAMPLE 6

This example illustrates that the action or the new hardeners in conventional binders such as gelatine is reinforced by the simultaneous presence of polymers which contain carboxyl groups. The carboxy group-containing polymer used is the sodium salt of a polyacrylic acid of low-molecular weight which was prepared as follows:

700 ml of water and 300 ml of n-propanol were added to 100 g of freshly distilled acrylic acid and the solution was adjusted to pH 7 with 10 % sodium hydroxide solution. 4 ml of 30 % hydrogen peroxide were added at room temperature and the solution was heated to 90°C with dilute sodium hydroxide. The temperature was kept at 90°C for a total of 4.5 hours, and further 4 ml of hydrogen peroxide were added after 2.5 hours. After cooling, ⅔ of the solvent were evaporated off under vacuum and the sodium polyacrylate was precipitated with ethanol and washed several times with the same solvent. It was then taken up in water and dialysed against tap water for 24 hours. The polymer solution was precipitated with ethanol after concentration by evaporation under vacuum, and it was then washed with ethanol until the polymer was no longer smeary. After drying under vacuum, 98 g of sodium polyacrylate (75 % of the theory) were obtained.

To 200 ml portions of a silver bromide emulsion containing 5.6 g of gelatine per 100 ml there were added A: 6.7 ml of a 5 % solution of sodium polyacrylate (corresponding to 3 % , based on gelatine) and B: 22.4 ml of the same solution (corresponding to 10 %, based on gelatine).

To obtain comparison sample C, 10 ml of water were added. In addition, 20 ml of a 5 % solution of di-n-butyl-naphthalene sulphonic acid sodium were added as wetting agent to each of the solutions.

8.5 μ thick layers of these solutions were formed on a 120 μ thick polyethylene terephthalate substrate by the immersion casting process and dried at 35°C.

6 samples of each of the individual layers A, B and C were then bathed in 1 % solutions of compounds 2, 3, 6, 7, 15 and 24 for 1 minute as indicated in example 2 and dried.

The results are summarised in the following table.

| Experimental series | | Melting point | Swelling factor | Wet strength (p) |
|---|---|---|---|---|
| Compound 2: | A (3%) | 10'100° | 2.9 | 1150 |
| | B (10%) | 10'100° | 3.2 | 1150 |
| | C — | 10'100° | 2.9 | 950 |

-continued

| Experimental series | | Melting point | Swelling factor | Wet strength (p) |
|---|---|---|---|---|
| Compound 3: | A (3%) | 10'100° | 2.6 | 950 |
| | B (10%) | 10'100° | 2.8 | 950 |
| | C — | 10'100° | 2.7 | 1050 |
| Compound 6: | A (3%) | 10'100° | 2.8 | 1050 |
| | B (10%) | 10'100° | 2.9 | 1000 |
| | C — | 10'100° | 3.0 | 1050 |
| Compound 7: | A (3%) | 10'100° | 2.0 | 950 |
| | B (10%) | 10'100° | 3.1 | 950 |
| | C — | 10'100° | 2.9 | 950 |
| Compound 15: | A (3%) | 10'100° | 2.9 | 1050 |
| | B (10%) | 10'100° | 3.2 | 1050 |
| | C — | 10'100° | 3.0 | 1050 |
| Compound 24: | A (3%) | 10'100° | 4.0 | 650 |
| | B (10%) | 10'100° | 4.2 | 850 |
| | C — | 10'100° | 4.3 | 650 |

From the results of the swelling factors determined in series A (addition of 3 % of polyacrylate) it is seen that the participation of the carboxyl groups of the polymer in the crosslinking reaction of the layer reduces the swelling factor.

We claim:

1. The method of hardening a light sensitive silver halide material having at least one layer which contains at least in part a protein-containing hydrophilic binder by contacting the protein-containing hydrophilic binder with an effective amount of a hardening compound to cause a crosslinking reaction of the protein molecules in the binder the improvement according to which the hardening compound is an alkyl ester of carboxylic acid selected of 1,2-dihydroquinoline-N-carboxylic acid and 1,2-dihydroisoquinoline-N-carboxylic acid, the 1,2-dihydroquinoline nucleus of which being alkoxy substituted in its 2-position and the 1,2-dihydroisoquinoline nucleus of which being alkoxy substituted in its 1-position.

2. The method of hardening a light sensitive silver halide material having at least one layer which contains at least in part a protein-containing hydrophilic binder by contacting the protein-containing binder hydrophilic with an effective amount of a hardening compound to cause a cross-linking reaction of the protein molecules in the binder the improvement according to which the hardening compound used is a compound of the following formulae:

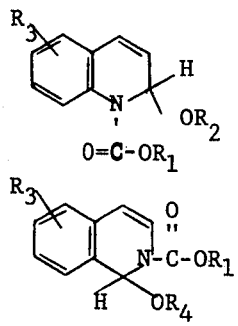

wherein $R_1$ represents an alkyl group containing up to 4 carbon atoms, $R_2$ represents an alkyl group containing up to 4 carbon atoms or a benzyl group or, when $R_3$ represents H, $R_2$ represents the group

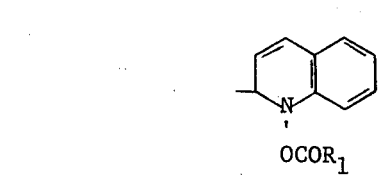

$R_3$ represents hydrogen, halogen, alkyl or alkoxy and $R_4$ represents an alkyl group.

3. Method according to claim 2 characterised by using a compound in which $R_3$ represents a hydrogen atom and $R_1$ represents methyl or ethyl.

4. Method according to claim 2, characterised in that the hardeners are contacted from aqueous solution.

5. Method according to claim 2, characterised in that the hardeners are contacted from alcoholic solution.

6. Method according to claim 2, characterised in that the hardeners are contacted from aqueous-alcoholic solution.

7. Method according to claim 2, characterised in that the hardeners are used in quantities of 0.5–5% by weight, based on the weight of the binder in a casting solution of the layer which is to be hardened.

8. Method according to claim 2, characterised in that the hardeners are applied as 0.2 – 10% solutions used as prehardening bath before the material is processed.

9. Method according to claim 2, characterised in that the layer which is to be hardened is coated with a 0.2–5% solution of the hardener and then dried.

10. The method as claimed in claim 1 wherein the photographic material is a multi-layered color photographic material.

11. The method as claimed in claim 2 wherein the binder is selected from the group consisting of gelatin, casein and zein.

* * * * *